Figure 1:
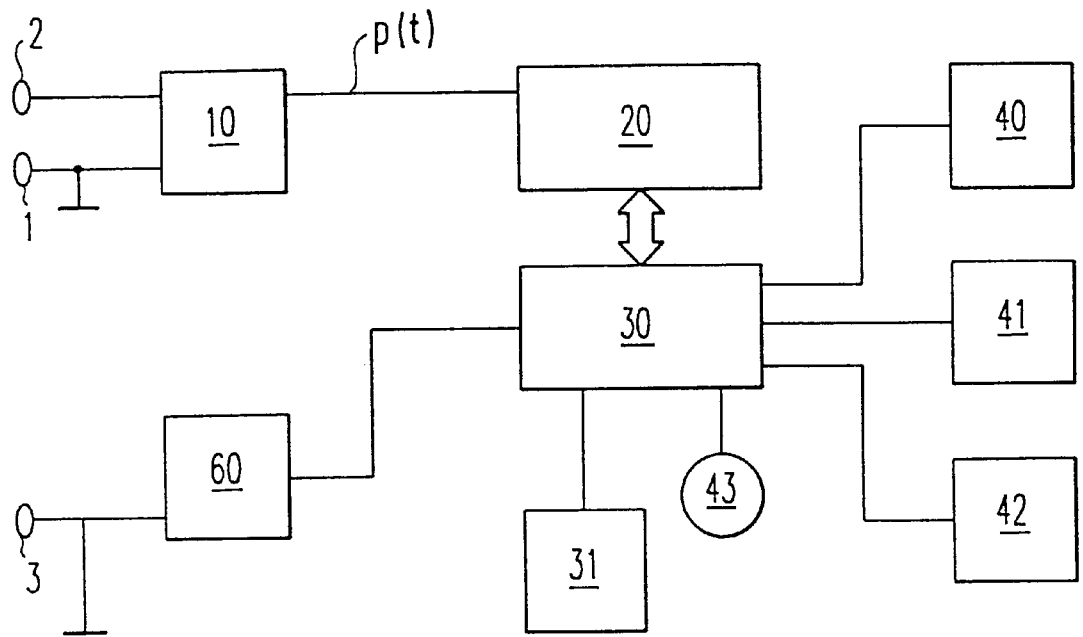

United States Patent [19]
Paulat

[11] Patent Number: 6,146,336
[45] Date of Patent: Nov. 14, 2000

[54] METHOD AND DEVICE FOR MEASURING THE INTRA-CRANIAL PRESSURE IN THE SKULL OF A TEST SUBJECT

[75] Inventor: Klaus Paulat, Blaustein, Germany

[73] Assignee: Nicolet Biomedical Inc., Madison, Wis.

[21] Appl. No.: 09/125,652

[22] PCT Filed: Feb. 20, 1997

[86] PCT No.: PCT/EP97/00815

§ 371 Date: Jan. 19, 1999

§ 102(e) Date: Jan. 19, 1999

[87] PCT Pub. No.: WO97/30630

PCT Pub. Date: Aug. 28, 1997

[30] Foreign Application Priority Data

Feb. 22, 1996 [DE] Germany .................... 196 06 687

[51] Int. Cl.$^7$ ...................................................... A61B 5/00
[52] U.S. Cl. ........................................... 600/561; 600/547
[58] Field of Search ................................. 600/547, 561, 600/587, 544; 73/717, 718, 719, 723, 724, 725

[56] References Cited

U.S. PATENT DOCUMENTS

| | | | |
|---|---|---|---|
| 4,425,920 | 1/1984 | Bourland et al. | 128/672 |
| 4,564,022 | 1/1986 | Rosenfeld et al. | 600/561 |
| 4,660,568 | 4/1987 | Cosman | 600/561 |
| 4,688,577 | 8/1987 | Bro | 600/504 |
| 4,893,630 | 1/1990 | Bray, Jr. | 600/561 |
| 4,971,061 | 11/1990 | Kageyama et al. | 600/438 |
| 4,984,567 | 1/1991 | Kageyama et al. | 600/438 |
| 5,074,310 | 12/1991 | Mick | 600/587 |
| 5,117,835 | 6/1992 | Mick | 600/587 |
| 5,617,873 | 4/1997 | Yost et al. | 600/561 |

FOREIGN PATENT DOCUMENTS

| | | |
|---|---|---|
| 31 30 326 A1 | 2/1983 | Germany . |
| WO 82/01122 | 4/1982 | WIPO . |

*Primary Examiner*—John P. Lacyk
*Assistant Examiner*—Charles Marmor, II
*Attorney, Agent, or Firm*—Westman, Champlin & Kelly, P.A.

[57] ABSTRACT

In order to detect the intra-cranial pressure in the skull of a test subject it is proposed to attach to the skull at least two electrodes in such a way that they have an electrical contact with the skull. Via a measuring device, the time curve of an electrical resistance and/or of a capacitance between the two electrodes is obtained as an electrical signal (p(t)). An extreme value of the electrical signal, following a blood pressure maximum according to a systole with a substantially uniform delay, is determined as a first amplitude value. A second amplitude value is obtained from the electrical signal (p(t)). This value is accepted at a point where the electrical signal has for the first time after the first amplitude value either a maximum or a turning point. A third amplitude value is obtained from the electrical signal after the second amplitude value. A standardized pressure measurement value is obtained from the amplitude values for further utilization. By means of this type of measurement it is possible to establish the intra-cranial pressure of a test subject in a simple, rapid and cost-effective manner, and to observe it even over lengthy periods, without thereby stressing the test subject.

35 Claims, 4 Drawing Sheets

METHOD AND DEVICE FOR MEASURING THE INTRA-CRANIAL PRESSURE IN THE SKULL OF A TEST SUBJECT

SPECIFICATION

The invention relates to a method and to a device for measuring an intra-cranial pressure in the skull of a test subject.

The intra-cranial pressure, i.e. the pressure within the skull of a human, is measured in many ways, all the measuring methods used at the moment being based on the fact that the skull, regarded as an enclosed container, must be opened by means of trepanning, in order to be able to insert an appropriate measurement receiver. The outlay on this is considerable, and probably needs no further explanation. In addition, the measurement results are only of restricted reliability, as the point of application of the drill hole, the type of measurement receiver itself and its condition which changes through time, and other peripheral conditions, can considerably influence the measurement results. Non-invasive measurements to date have been exclusively carried out on children, whose fontaelle is not yet closed, so that the scalp movement in this area, which is in fact a measurement of the fluctuations in pressure, can be measured. An atromatic measurement of the intra-cranial pressure by taking a so-called "capacitive pulse wave" is known from Wiener klinische Wochenshrift, Volume 18, 28 September 1990, pages 543–547. It has however become apparent that the known method of measurement provides considerable difficulties as regards its reproducibility.

As further possibilities of non-invasive measurement of the intra-cranial pressure, there are described measurement of sound transmission through the skull (Annals of Biomedical Engineering, Volume 23, pages 720,727,1995), measurement of the thickness of the meninges (Neuroscience Letters 198, pages 68–70, 1995) or also a type of volumetric measurement via ultrasound (NASA Tech. Briefs, June 1994). All these known methods are however complex and their results offer little satisfaction.

The object underlying the invention is to indicate a method and a device for measuring the intra-cranial pressure, which in a simple way permits an adequately accurate determination of the intra-cranial pressure.

This object is achieved by a method for measuring the intra-cranial pressure in a skull of a test subject, which comprises the following steps:

At least two electrodes are attached to the skull of the test subject in such a way that they have electrical contact with the skull. A chronological progress of an electrical resistance, particularly of a complex resistance, i.e. an ohmic resistance, and of a capacitance between the at least two electrodes, is obtained as an electrical signal. An extreme value following the maximum blood pressure corresponding to a systole, with a substantially uniform delay of the electrical signal is determined as a first amplitude value. A second amplitude value is obtained from the electrical signal, where this has either a maximum or a turning point for the first time after the first amplitude value. A third amplitude value is obtained from the electrical signal at a point in time later than the second amplitude value. A standardized pressure measurement value is obtained from the amplitude values for further use. An essential point of this method resides on the one hand in the fact that in a particularly simple way and by means of previously known methods, a measurement is undertaken which may be carried out at any time by non-specialist personnel. Whereas nowadays in practical medicine measurement of brain pressure is usually carried out epidurally by means of miniaturized pressure probes, i.e. can be carried out only by doctors, the method according to the invention can be carried out by any medical orderly, even in an ambulance. The measurement values obtainable by means of the method according to the invention can be further used in many ways. In particular, it is possible to trace alterations in the brain pressure over lengthy periods of time, without the test subject or patient being stressed thereby.

A quotient can be formed from the second amplitude value and the third amplitude value, in order to obtain the standardized pressure measurement value. In this way it is ensured that the dispersions unavoidably incurred during measurement of the absolute values, due to the most varied influences such as physical differences, varying electrode applications, etc., have no influence on the measurement results.

Another possibility of obtaining standardized pressure measurement values resides in the formation of a vector in such a way that the vector is formed from a start point at the second amplitude value and an end point at the third amplitude value. In particular, the direction of the vector plays a part in calculating the pressure measurement value. This also applies when the vector is formed from a start point in the first and an end point in the second amplitude value.

In a preferred embodiment, the third amplitude value is derived from the electrical signal at a specific span of time after the second amplitude value. This specific span of time can now be obtained from a time interval between the second amplitude value and a fourth amplitude value. The fourth amplitude value is defined at a point where the progress of the electrical signal has a curvature opposed to the progress of the electrical signal over time in the second amplitude value. The abovementioned specific span of time preferably substantially comes to half the time interval.

Preferably, the measurement values are derived not from individual events, but from average signal values, which have been averaged over a plurality of electrical signals. In this way, in a way known per se, the measurement accuracy is considerably increased.

In an embodiment of the invention, the first amplitude value is used as a repeating start point in time for forming the average signal value. It is however particularly advantageous to attach a further electrode to the test subject in order to obtain an ECG, which is in any case necessary in most cases, and to define a value in the ECG, which is used as a repeating start point in time for forming the average signal values.

In order to calibrate the measurement, preferably a first and second (standardized) pressure measurement value are obtained and in fact the first pressure measurement value in a first, and the second pressure measurement value in a second position of the test subject, the skull of the test subject lying in the first position relative to the spatial position of his heart (particularly his right atrium) by a defined amount higher (or lower) than in the second position. By means of this extremely simple alteration in the hydraulic conditions, absolute measurements can now be carried out.

The electrodes for obtaining the electrical signal are preferably attached at positions of the skull of the test subject which lie as far apart as possible. For this reason, one electrode is preferably attached in the area of the hairline of the forehead of the test subject, and the further electrode in the area behind his ear. It has become apparent that the signals thus obtained are optimally usable. One of the two electrodes in this case is passed to earth, the electrode passed to earth preferably also simultaneously forming the earth electrode for an ECG derivation.

The device according to the invention is characterized by the following features:

- at least two electrodes (1,2) which are attachable to the skull of the test subject in such a way that they have an electrical contact with the skull;
- a measuring device (10) for obtaining an electrical signal (p(t)) which represents a time curve of an electrical resistance and/or of a capacitance between the at least two electrodes (1,2);
- a storage device (20) for storing the electrical signal (p(t));
- a computer device (30) for determining an extreme value of the electrical signal (p(t)), which follows a blood pressure maximum corresponding to a systole with a substantially uniform delay, and for determining a first amplitude value (Pmin) of the extreme value and to determine a second amplitude value (P1) from the electrical signal (p(t)), at the point where the electrical signal (p(t)) has for the first time after the first amplitude value (Pmin) either a maximum (.p(t))=0) or a turning point (..p(t))=0) and is used to obtain a standardized pressure measurement value from the amplitude values (Pmin, P1,P2), and
- utilization devices, particularly a display device (40) a printer (41) and/or a writing station for writing out from data carriers.

Further preferred embodiments of the invention will become apparent from the sub-claims.

Figure 2:
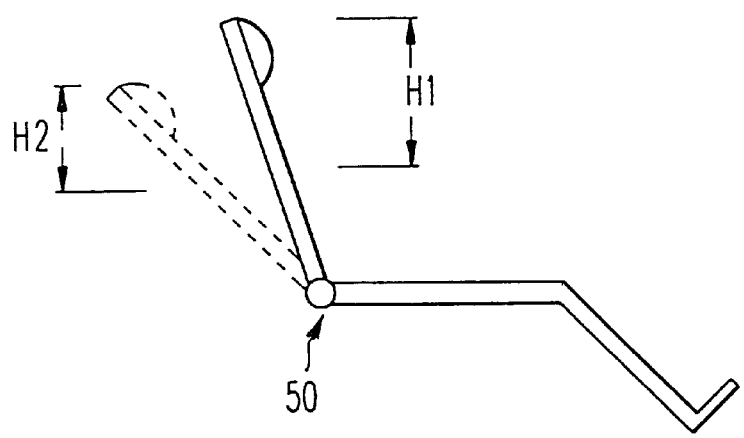
Figure 3:
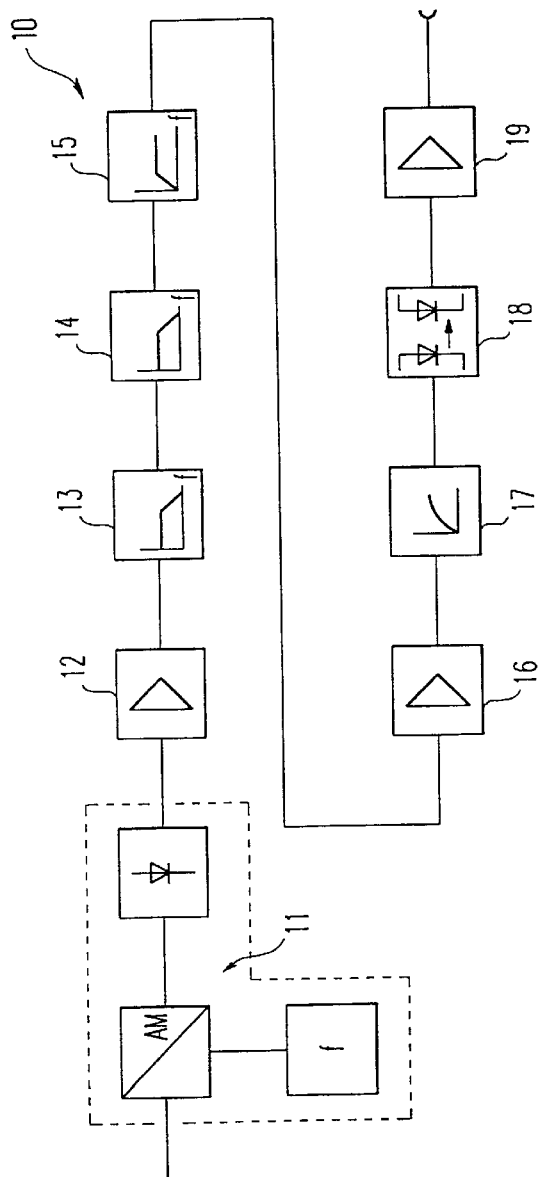
Figure 4:
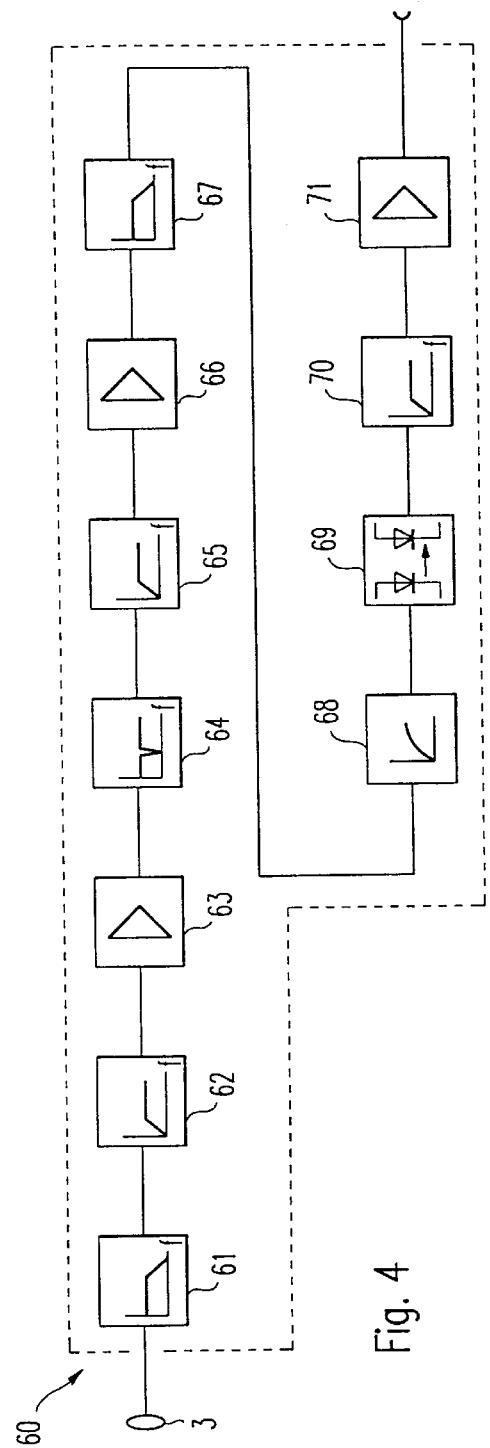
Figure 5:
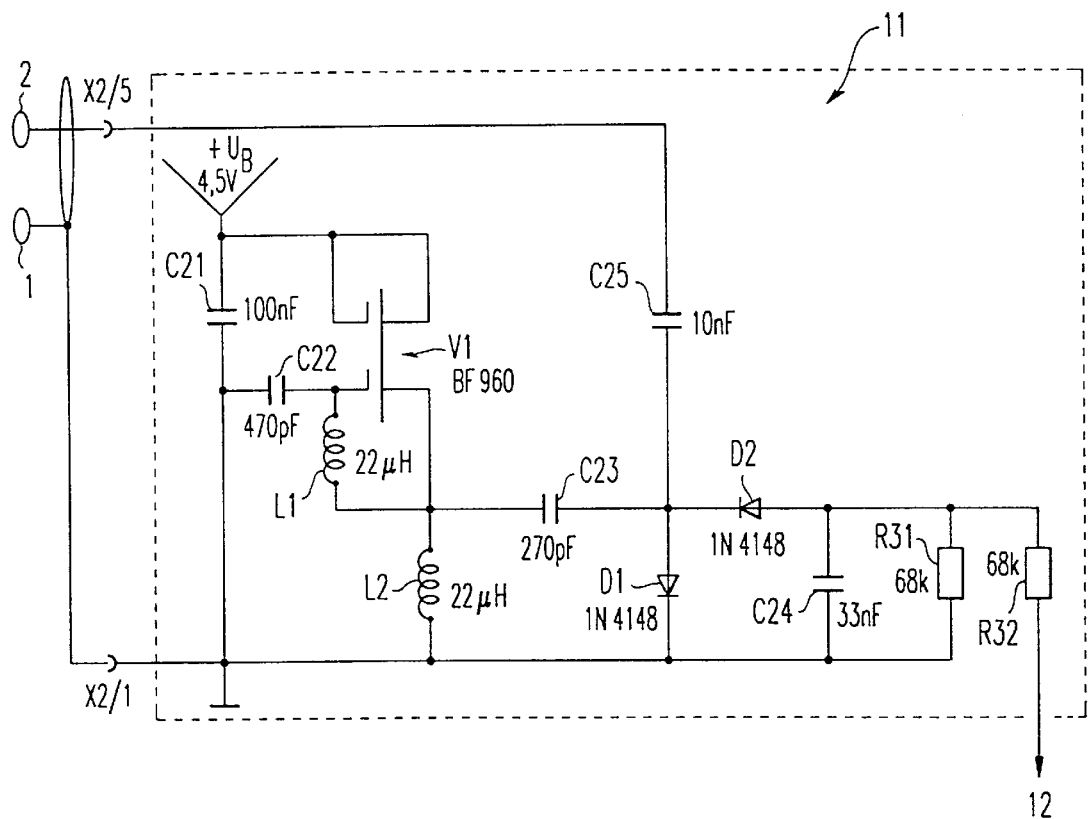
Figure 6:
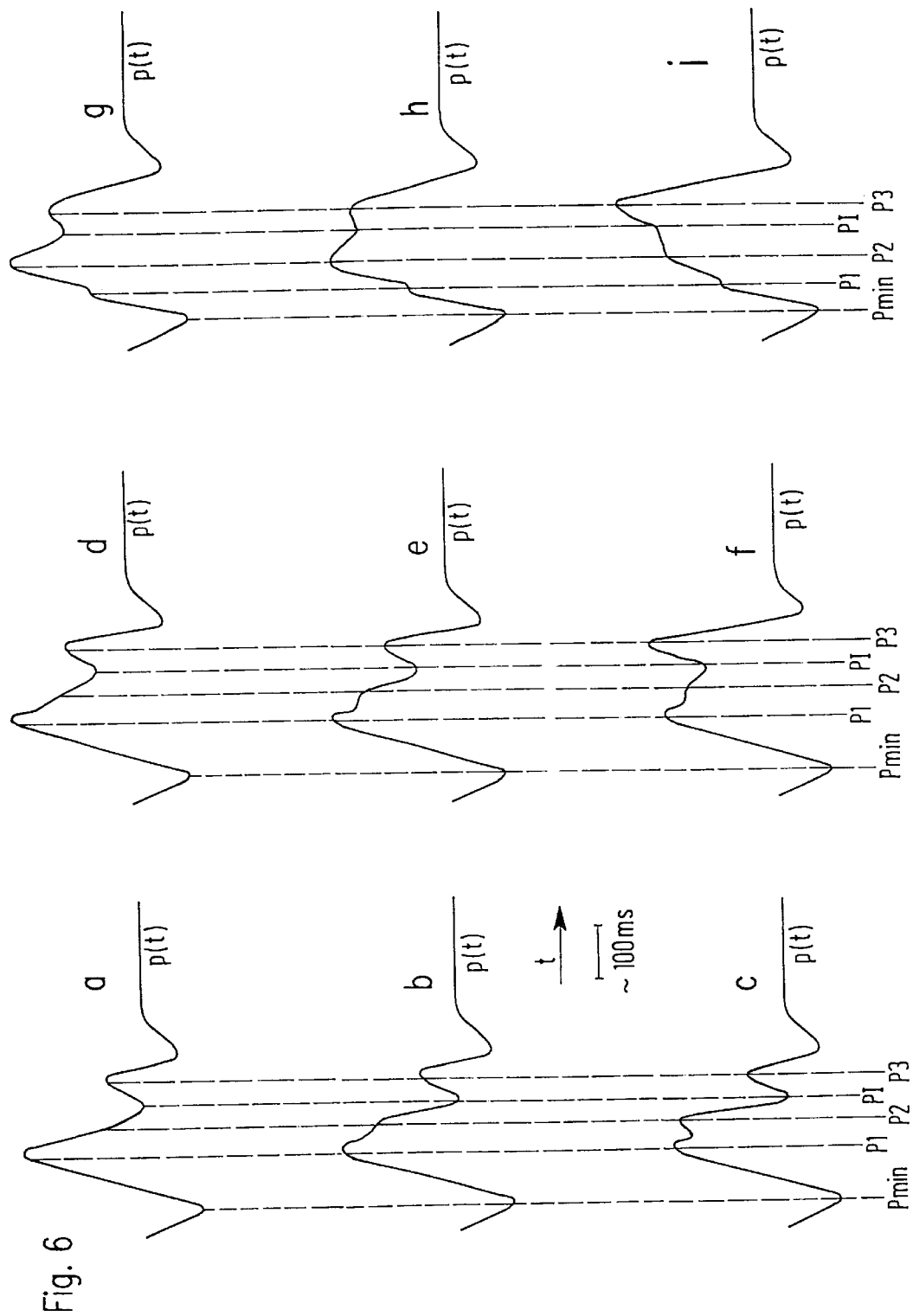

The invention is explained in more detail in the following with reference to drawings, which show:

FIG. 1: a block circuit diagram of an embodiment of a device for measuring the intra-cranial pressure in the skull of a test subject;

FIG. 2: a calibrating device;

FIG. 3: a block circuit diagram of a portion of the measuring arrangement shown in FIG. 1;

FIG. 4: a block circuit diagram of a further portion of the arrangement shown in FIG. 1;

FIG. 5: a detail circuit diagram of a portion of the arrangement shown in FIG. 3;

FIG. 6: measurement data which can be obtained by an arrangement according to FIG. 1;

Identical parts or those with identical functions are provided in the following description with the same reference numbers.

As FIG. 1 shows, the device comprises a measuring device 10, at the input of which there lie an earth electrode 1 and a by-pass electrode 2. The earth electrode 1 in this case is attached for example behind one ear of the test subject, the by-pass electrode 2 on the forehead in the vicinity of the hairline, obliquely opposite the earth electrode 1 in such a way that the greatest possible spacing exists between the electrodes 1 and 2.

The output voltage p(t) of the measuring device 10 is passed to a store of average 20, which is in a controlling and controlled connection with a computing device 30. Also supplied to the computing device 30 is an output signal from an ECG amplifier 60, one input of which likewise is passed to earth, (or to the earth electrode 1), and the other output of which is coupled to an ECG electrode 3 constructed and attached in a conventional way.

The computing device 30 is further connected to a timer 31 and to data output devices, in this case a CRT 40, a printer 41 and a diskette station 42 are provided in order to illustrate the possibilities of output. In addition, an alarm device 43 is coupled to the computing device 30, said alarm device being set in operation when the scanned measurement values fulfil specific criteria.

FIG. 2 indicates a retaining device 50, upon which a test subject can be seated. In a first upright position of a back-rest of the retaining device 50 (shown in FIG. 2 by a continuous line) there is a first vertical difference H1 between his skull and the heart, while in a second, leaning position (indicated in FIG. 2 by broken lines), a second, smaller vertical difference H2 is present between the heart and the skull. This retaining device 50 serves to predetermine a defined pressure differential, in order to calibrate the whole arrangement.

The measurement device 10 shown in FIG. 1 will be explained in more detail in the following with reference to FIG. 3.

The measurement device 10 comprises a modulator/demodulator portion 11, in which a carrier frequency f is amplitude-modulated and rectified in dependence on the ohmic and in particular capacitive conditions existing between the electrodes 1 and 2. The rectified output signal of the modulator/demodulator 11 is passed to an amplifier or voltage doubler 12, which is followed by a first low-band-pass filter 13 with an upper threshold frequency of about 71 Hz for restricting the frequency of the utility signal, a second low-band-pass filter 14 for suppressing the already mentioned carrier frequency f and a high-band-pass filter 15, whose threshold frequency can be switched between the values 7.9 MHz and 450 MHz, and which serves to suppress disturbances in the utility signal.

Following the high-band-pass filter 15, as an amplifier 16 whose amplification is adjustable within a wide range. In the embodiment shown here, an amplification factor of K-23-230 is provided.

Following the amplifier 16 is a linearizing circuit 17, which is matched to the transmission characteristic of an ortocoupler 18, which serves for galvanic separation. Following the ortocoupler 18 is an impedance transformer 19.

The ECG amplifier 60 will be explained in more detail in the following with reference to FIG. 4, although this ECG amplifier can be of a previously known constructive type known per se.

The ECG amplifier 60 comprises at the input side a low-band-pass filter 61, to the input of which the ECG electrode 3 is connected. The low-band-pass filter 61 has a threshold frequency of about 34 Hz and serves for HF suppression.

Following the low-band-pass filter 61 is a high-band-pass filter 62, whose threshold frequency lies at about 0.16 Hz and which serves for DC suppression. At the output of the high-band-pass filter 62 there is an ECG preamplifier 63, whose amplification factor in the embodiment shown here is adjustable between 16 and 150, and whose output signal is applied to the input of a Notch filter 64, which suppresses the main frequency (50 or 60 Hz) used at the site of use.

The output signal of the Notch filter 64 is applied to the input of a high-band-pass filter 65, which has the same properties and serves the same purpose as the high-band-pass filter 62.

The output signal of the high-band-pass filter 65 is passed to the input of an ECG amplifier 66 with a constant amplification factor (here K=33). The output signal of the ECG amplifier 66 is passed to the input of a low-band-pass filter 67 with a threshold frequency of about 32 Hz, which serves to suppress harmonic waves. The output signal of the low-pass-band 67 is passed to a linearizing circuit 68, which is matched to the characteristic of a following ortocoupler 69, which serves for galvanic separation. The output signal of the ortocoupler 69 is passed to the input of a high-band-pass filter 70, which serves for DC suppression, and has a threshold frequency of about 0.22 Hz. The output signal of the high-band-pass filter 70 is passed to the input of an impedance transformer 71, whose output signal, as shown in FIG. 1, is passed to the computer circuit 30.

The modulator/demodulator device 11 shown in FIG. 3 in the block circuit diagram, will be explained in more detail in the following with reference to FIG. 5.

As can be seen from FIG. 5; the modulator/demodulator device 11 comprises a field-effect transistor V1 with two gates, one gate, together with the drain connection, being at the positive operating voltage, and the other gate being connected to earth via a capacitor C22. The two gate connections are connected together via a capacitor C21.

The second gate connection furthermore lies via a first inductance L1 at the source connection of the transistor V1, which in turn is connected to earth via a second inductance L2 of the same size. The source connection is passed via a capacitor C23 to the anode of a first diode D1, whose cathode is connected to earth. The anode of the first diode D1 is furthermore connected with the cathode of a second diode D2, the anode of which is passed via a resistor R32 to the output of the modulator/demodulator circuit 11, i.e. to the input of the amplifier 12. The anode of the second diode D2 is furthermore led to earth via a parallel circuit of a capacitor C24 and a resistor R31.

The connection point of the two diodes D1 and D2 of the capacitor C23 is passed via a capacitor C25 to the input of the modulator/demodulator circuit 11, i.e. to the by-pass electrode 2.

The circuit shown in FIG. 5 functions in such a way that a frequency predetermined by the inductances L1 and L2 and the capacitor C22 is generated as a specific amplitude, whose amplitude is altered by the complex resistance, which is applied between the electrodes 1 and 2, the capacitance principally between the electrodes 1 and 2 playing a part with respect to the amplitude modulation mentioned.

It should be expressly mentioned at this point that it is possible to use not only one measurement of the capacitance between the electrodes 1 and 2 but also the real ohmic resistance between the two electrodes or alternatively a combined measurement of these two magnitudes according to the present invention.

In the following the method according to the invention will be explained in more detail with reference to FIG. 6, which represents measurements on nine test subjects in all. In this case there is allocated to each test subject a letter a—e. Each of the individual views a–e comprises a plurality of averaged overflows, the start point in time of formation of the average value being derived from an ECG (obtained with the ECG amplifier 60). The representation of all the curves in this case is such that the signals p(t) are recorded from a point in time onwards which lies briefly before a first and absolute minimum value Pmin in the signal p(t). The scale indicated in FIG. 6 is only indicated for coarse assessment of the actual conditions, as the absolute values are not involved in the representation shown here.

The curves a–c in FIG. 6 shows all the signal curves in test subjects whose intra-cranial pressure can be termed normal. Such "normal curves" are initially characterized in that there is a substantially flat curve configuration between the first significant amplitude value Pmin, the first minimum shown in FIG. 6 and the second significant amplitude value P1.

After the second amplitude value, the maximum at P1, a third amplitude value P2 can be defined, which lies roughly in the center between the second amplitude value P1 and a fourth amplitude value PI, which is defined at a local minimum with a subsequent maximum value P3. In the three curves a–c it can be seen that the third amplitude value P2 can lie both within a smooth (declining) curve branch and also in a turning point (curve b) or even at a maximum (curve c). In all cases however, the signal P(t) at P2 is smaller than at P1.

The curves d–f which show signal curves p(t) which represent test subjects with an increased intra-cranial pressure, differ from the curves a–c in that the signal configuration of p(t) at the amplitude value P3 is increased. Otherwise, here also the amplitude values P2 are lower than the amplitude values P1.

The image of the signal curves P(t) is quite different, which have been derived from test subjects with an increased intra-cranial pressure, as are to be found in the views in FIGS. 6 g–i. In all these representations it can be seen that the third amplitude value P2 is always higher than the second amplitude value P1. The fourth amplitude value PI can be even higher than the third amplitude value P2. This means that the second amplitude value P1 appears rather as a turning point than as a (local) maximum, so that when forming the quotient P2/P1, one obtains a (standardized) value there for, whether a "normal" or an "abnormally increased" intra-cranial pressure predominates, which is the case when this ratio exceeds the number 1. When this is the case, particularly when the extent by which this value 1 is exceeded lies outwith a permissible range, the alarm device 43 shown in FIG. 1 can be triggered.

Furthermore it is also possible to undertake the vectorial representation already described, in order to establish whether the third amplitude value P2 is higher than the second amplitude value P1. This is regularly the case when the gradient of the vector from P1 to P2 becomes greater than zero. Another possible way of analyzing the curve in a simple way resides in forming the second derivation p(t), which in the curve configuration g–i has the value zero at the amplitude value P1. In addition, the time intervals between the first amplitude value Pmin and the second amplitude value P1 are lower than in the curves a–f, as is clearly seen from FIG. 6.

When one observes the intra-cranial pressure of a test subject, i.e. wishes to establish whether the pressure is increasing with time, which could indicate specific injuries, it is of advantage if a calibration is undertaken. Then measurement signals are derived from the test subject in two different positions, in a first position the head lying higher relative to the heart than in a second position. By means of such tilting, the intra-cranial pressure can be brought from a normal value (a healthy test subject stands upright) according to FIG. 6a to a curve according to FIGS. 6 g–i, when the head of the test subject is located extremely low, the test subject for example doing a headstand. Such a curve should naturally never occur when the test subject is sitting or lying.

LIST OF REFERENCE NUMBERS 1 earth electrode
2 by-pass electrode
3 ECG electrode
10 measuring device
11 modulator/demodulator circuit
12 amplifier
13 low-band-pass (71 Hz)
14 low-band-pass (suppression f)
15 high-band pass 7.9 MHz/0.45 Hz
16 amplifier 17 linearization
18 galvanic separation
19 impedance transformer
20 store
30 computer device
31 timer
40 CRT
41 printer
42 diskette station
43 alarm device
50 retaining device
60 ECG amplifier
61 low-band-pass 34 Hz, HP suppression
62 high-band pass 0.16 Hz, DC suppression
63 ECG preamplifier
64 Notch filter
65 high-band-pass, DC suppression
66 ECG amplifier
67 low-band-pass 32 Hz, harmonic wave suppression
68 linearization
69 galvanic separation
70 high-band-pass DC suppression, 0.22 Hz
71 impedance transformer

What is claimed is:

1. Method of measuring an intra-cranial pressure (ICP) in the skull of a test subject, comprising the steps:

attaching two electrodes to the skull of the test subject in such a way that the electrodes have an electrical contact with the skull;

obtaining a time curve of an electrical parameter between the two electrodes as an electrical signal (p(t));

determining an extreme value of the electrical signal following a maximum in blood pressure corresponding to a systole with a substantially uniform delay as a first amplitude value (Pmin);

obtaining a second amplitude value (P1) from the electrical signal (p(t)), where this has for the first time after the first amplitude value (Pmin) either a maximum (.P(t)=0) or a turning point (..p(t)=0);

obtaining a third amplitude value (P2) from the electrical signal after the second amplitude value;

obtaining a standardized pressure measurement value from the amplitude values (Pmin, P1, P2) for further utilization.

2. Method of claim 1 wherein the electrical parameter comprises capacitance.

3. Method of claim 1 wherein the electrical parameter comprises resistance.

4. Method of claim 1 wherein the electrical parameter comprises resistance and capacitance.

5. Method according to claim 1, wherein a quotient (P2/P1) is formed from the second amplitude value (P1) and the third amplitude value (P2) in order to obtain the standardized pressure measurement value.

6. Method according to claim 1, wherein in order to form a vector a start point is formed for the vector at the second amplitude value (P1) and an end point for the vector at the third amplitude value (P2), and the standardized pressure measurement value is formed from the vector.

7. Method according to claim 1, wherein in order to form a vector a start point for the vector is formed at the first amplitude value (Pmin) and an end point for the vector is formed at the second amplitude value (P1) and the standardized pressure measurement value is formed from the vector.

8. Method according to claim 1, wherein a period of time is defined after the second amplitude value (P1), after which the third amplitude value (P2) is scanned from the electrical signal (p(t)).

9. Method according to claim 8, wherein the curve of the electrical signal (p(t)) is investigated over time and a fourth amplitude value (PI) is defined at a point where the curve of the electrical signal over time has an opposed curvature to the curve of the electrical signal over time at the second amplitude value (P1), and the defined span of time being derived from the time interval between the second amplitude value (P1) and the fourth amplitude value (PI).

10. Method according to claim 9, wherein the defined span of time comes to substantially half the time interval.

11. Method according to claim 1, wherein in order to form an average signal value, an average is taken from a plurality of electrical signals (p(t)).

12. Method according to claim 11, wherein the first amplitude value (Pmin) is used as a repeating start point in time for forming the average signal value.

13. Method according to claim 11, wherein at least one further electrode is attached to the test subject in order to obtain an ECG, and a value in the ECG is defined, which is used as a repeating start point in time for forming the average signal value.

14. Method according to claim 1, wherein in order to calibrate the measurement, at least one first and one second standardized pressure measurement value are obtained in at least one first and one second position of the test subject, the skull of the test subject in the first position being higher by a specific quantity relative to the spatial position of the heart of the test subject, particularly the right atrium of the heart, than in the second position.

15. Method according to claim 1, wherein the at least two electrodes are attached at positions on the skull of the test subject which lie as far apart as possible.

16. Method according to claim 15, wherein one electrode is attached in the region of the hairline of the forehead of the test subject, and one electrode in the area behind one ear of the test subject.

17. Method according to claim 1, wherein one of the at least two electrodes is connected to a ground electrode.

18. Method according to claim 17, wherein the ground electrode forms an electrode for simultaneous ECG derivation.

19. Device for measuring an intra-cranial pressure (ICP) in the skull of a test subject, comprising:

at least two electrodes which are attachable to the skull of the test subject in such a way that the electrodes have an electrical contact with the skull;

a measuring device for obtaining an electrical signal (p(t)) which represents a time curve of an electrical parameter between the at least two electrodes;

a storage device for storing the electrical signal (p(t));

a computer device for determining an extreme value of the electrical signal (p(t)), which follows a blood pressure maximum corresponding to a systole with a substantially uniform delay, and for determining a first amplitude value (Pmin) of the extreme value and to determine a second amplitude value (P1) from the electrical signal (p(t)) at the point where the electrical signal (p(t)) has for the first time after the first amplitude value (Pmin) either a maximum ((.p(t))=0) or a turning point ((..p(t))=0), and to determine a third amplitude value (P2) from the electrical signal (p(t)) after the second amplitude value (P1), and is used to obtain a standardized pressure measurement value from the amplitude values (Pmin, P1, P2); and utilization devices selected from the group including a display device, a printer, and a writing station for writing out from data carriers.

20. Device of claim 19 wherein the electrical parameter comprises capacitance.

21. Device of claim 19 wherein the electrical parameter comprises resistance.

22. Device of claim 19 wherein the electrical parameter comprises resistance and capacitance.

23. Device according to claim 19, wherein the computer device is configured such that a quotient (P2/P1) is formed from the second amplitude value (P1) and the third amplitude value (P2), in order to obtain the standardized pressure measurement value.

24. Device according to claim 19, wherein the computer device is configured such that in order to form a vector, a start point is formed for the vector at the second amplitude value (P1) and an end point for the vector is formed at the third amplitude value (P2), and a standardized pressure measurement value is formed from the vector.

25. Device according to claim 19, wherein the computer device is configured such that, in order to from a vector, a start point for the vector is formed at the first amplitude value (Pmin) and an end point for the vector is formed at the second amplitude value (P1), and the standardized pressure measurement value is formed from the vector.

26. Device according to claim 19, comprising a time-determining device for determining time after the second amplitude value (P1), the computer device being configured such that the third amplitude value (P2) is scanned from the electrical signal after a predetermined span of time.

27. Device according to claim 26, wherein the computer device is configured such that the curve of the electrical signal (p(t)) over time is investigated, and a fourth amplitude value (PI) is defined at a point where the curve of the electrical signal over time has a curvature opposed to the curvature of the electrical signal over time at the second amplitude value (P1), and the computer device further being configured such that the defined span of time is derived from the time interval between the second amplitude value (P1) and the fourth amplitude value (PI).

28. Device according to claim 27, wherein the time-determining device is configured such that the defined time span comes to substantially half the time interval.

29. Device according to claim 19, wherein the measuring device, the storage device and the computer device are configured to form an average signal value from a plurality of electrical signals (p(t)).

30. Device according to claim 29, wherein the computer device is configured such that the first amplitude value (Pmin) can be obtained as a repeating start point in time for forming the average signal value.

31. Device according to claim 29, wherein a further electrode and a measuring device attached thereto are provided in order to obtain an ECG, the computer device being configured such that a value in ECG is defined which is used as a repeating start point in time for forming the average signal value.

32. Device according to claim 19, comprising a retaining device for supporting the test subject in at least two positions, the skull of the test subject in the first position lying by a specific amount higher relative to the spatial position of the right atrium of the heart of the test subject than in the second position, in such a way that in order to calibrate the measurement at least a first and a second standardized pressure measurement value can be obtained in the first and in the second positions.

33. Device according to claim 19, wherein the at least two electrodes are configured such that the electrodes are attachable at two positions of the skull of the test subject which lie as far apart as possible.

34. Device according to claim 33, wherein one electrode of the at least two electrodes is connected to a ground electrode.

35. Device according to claim 34, wherein the electrode connected to ground is applied to an ground input of a measuring device in order to obtain an ECG.

* * * * *